United States Patent [19]

Shallman

[11] Patent Number: 5,693,069

[45] Date of Patent: Dec. 2, 1997

[54] GALLBLADDER STONE EXTRACTING FORCEPS FOR LAPAROSCOPIC CHOLECYSTECTOMY

[76] Inventor: Richard W. Shallman, 118 High Meadows, Richland, Wash. 99352

[21] Appl. No.: 538,744

[22] Filed: Oct. 3, 1995

Related U.S. Application Data

[63] Continuation-in-part of Ser. No. 10,725, Jul. 15, 1993.

[51] Int. Cl.⁶ .......................... A61B 17/28; A61B 17/42; A61B 17/44
[52] U.S. Cl. .......................... 606/205; 606/110; 606/207
[58] Field of Search .................................. 606/110, 111, 606/205, 206, 207, 210

[56] References Cited

U.S. PATENT DOCUMENTS

| | | |
|---|---|---|
| 229,724 | 12/1880 | Ericson et al. . |
| 265,683 | 8/1882 | Drummond et al. . |
| 1,127,948 | 2/1915 | Wappler . |
| 1,725,173 | 8/1929 | Anderson . |
| 2,034,785 | 3/1936 | Wappler . |
| 2,113,246 | 4/1938 | Wappler . |
| 2,597,394 | 5/1952 | Snowden . |
| 3,022,787 | 2/1962 | Daniel . |
| 3,209,753 | 10/1965 | Hawkins et al. . |
| 4,088,134 | 5/1978 | Mazzariello . |
| 4,300,564 | 11/1981 | Furihata . |
| 4,509,517 | 4/1985 | Ziblein . |
| 4,632,110 | 12/1986 | Sanagi . |
| 4,807,626 | 2/1989 | McGirr . |
| 4,811,735 | 3/1989 | Nash et al. . |
| 5,147,369 | 9/1992 | Wagner . |
| 5,207,702 | 5/1993 | Pearl . |
| 5,320,637 | 6/1994 | Borders . |

OTHER PUBLICATIONS

Jarit, the instrument people, Endoscopic Instrumentation, By J. Jamner surgical instruments, inc., 1992.

Lorè, J.M., Tender Grip Forceps, American Journal of Surgery, (1962), vol. 174, pp. 84–85.

Jarit, The Instrument People, Endoscopic Instrumentation, (1992), pp. 24–25.

Aloe Medical Catalog, (1965), pp. 83, 95.

Codman Catalog of Surgical Instruments, (1984), pp. 135, 180.

Sklar Products Quality Surgical Instruments Catalog, (1982), pp. 70, 334.

Odess Local Health Centre, Derwent Publications Ltd., (1993) Surgical clamp for laser irradiation of tissue–consists of jaws with spiral laser beam slit reducing trauma, (1993).

*Primary Examiner*—Robert A. Hafer
*Assistant Examiner*—Justine R. Yu
*Attorney, Agent, or Firm*—Dewitt Ross & Stevens SC

[57] ABSTRACT

Forceps for grasping, crashing, and removing gallstones from the opened neck of a gallbladder which is extracted through an abdominal port site during laparoscopic surgery. The forceps include upper arms having shallow concave oval tips which include a narrower distal region, a wider central region, and a narrow proximal region. The upper arms are bowed slightly outward to allow the tips to be spring-biased against each other, or against an object held between the tips.

15 Claims, 2 Drawing Sheets

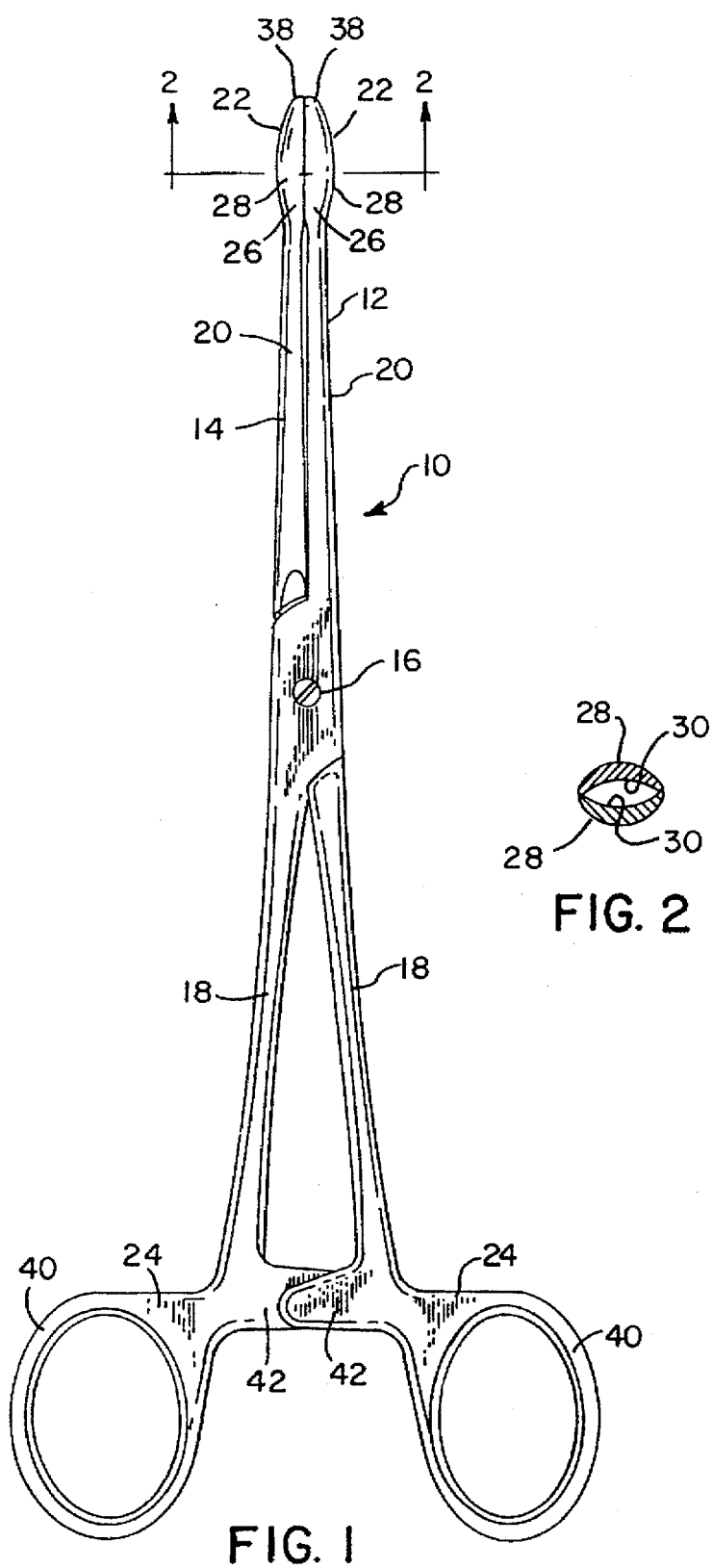
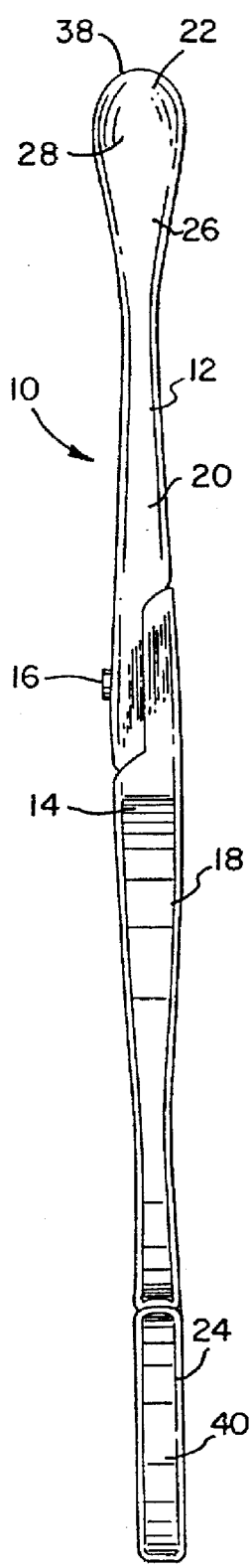
FIG. 1
FIG. 2
FIG. 3

GALLBLADDER STONE EXTRACTING FORCEPS FOR LAPAROSCOPIC CHOLECYSTECTOMY

RELATED APPLICATION

This is a continuation-in-part of U.S. patent application Ser. No. 29/010,725 filed on 15 Jul. 1993, now abandoned, entitled GALLBLADDER STONE FORCEPS, the entirety of which is incorporated by reference.

FIELD OF THE INVENTION

The present invention relates generally to surgical forceps, and more specifically to surgical forceps which are particularly adapted to grasping, crushing and removing gallstones from the opened neck of a gallbladder being extracted from an abdominal port site during laparoscopic cholecystectomy.

DESCRIPTION OF THE PRIOR ART

The gallbladder is a piriform (i.e., pear-shaped) sac that lies within a shallow valley on the lower portion of the liver, and which concentrates the liver's bile to aid in the digestion and absorption of fats. Occasionally, cholesterol crystallizes within the gallbladder, forming stony masses or concretions of crystals known as gallstones. These gallstones can grow to be as large as golf balls, or even larger. The stones cause intimation and pain, and can result in infection of the gallbladder. If the stones pass into the bile ducts, they can cause jaundice, pancreatitis, or even death. If symptomatic gallstones are detected, removal of the diseased gallbladder and stones is generally recommended.

Removal of the gallbladder and stones is generally done by a procedure known as laparoscopic cholecystectomy. Operating ports are made in the abdomen for the insertion of laparoscopic instruments, and a laparoscopic camera allows the surgeon to view the interior of the abdominal cavity on a video monitor. The gallbladder is dissected free and is pulled to an abdominal port site. The narrow end (neck) of the gallbladder (or another portion of the gallbladder) is grasped with a clamp and pulled through the abdominal port site. A small hole is then made in the portion of the gallbladder that has been pulled through the port, the bile is sucked out, and the gallbladder is extracted from the abdomen.

Problems arise if the gallbladder and its associated stones are too large for extraction. The abdominal port site can be enlarged, but this is contrary to the goals of minimally invasive surgery. It is instead preferable to remove the stones and debris from the gallbladder, allowing its removal without enlarging the abdominal port site. However, it can be quite difficult to remove the stones from the gallbladder and/or the gallbladder from the body if the gallbladder has large or impacted stones, or a congealed mass of stones. If this is the case, the operator must select a tool to remove the stones or break them into smaller fragments for removal.

The crushing or extraction of large stones presents several problems. Generally, the stone extraction devices are long and narrow so that they may more easily fit within the patient's body. This tends to make the devices too small and flimsy to crush stones, and additionally they may be so slender that they can easily puncture the walls of the gallbladder if they are not delicately handled. As a result, the operator must often take time during the course of the operation to exchange the lightweight extraction devices with heavier crushing devices.

However, the stone crushing devices of the prior art are flawed as well. Because stone crushing devices must provide sufficient strength and leverage to crush the stones, they are generally larger than stone removal devices, and the operator may need to make a larger port in the body and/or in the gallbladder to accommodate the stone-crushing device. Additionally, the time required for the exchange of tools and the adjustments made to the body to accommodate these tools requires that the patient spend a longer time under anesthesia. Consequently, abdominal port site enlargement is often utilized, requiring efforts to close the enlarged abdominal port site opening and prolonging the time needed for the patient's recovery.

There are several devices in the prior art for facilitating the removal of gallbladder stones or other types of stones, such as kidney stones and the like. A summary of some of the salient features of these inventions is given below.

Initially, there are electronic and/or automatic devices for removing stones, such as those illustrated in U.S. Pat. No. 4,902,276 to Zakko and U.S. Pat. No. 4,811,735 to Nash et al. However, due to the manufacturing expense and operational complexity of these devices, they are not favored for use in the removal of stones. Rather, manual stone extractors are most commonly used for the removal of stones owing to their relatively low cost and their ease of operation and cleaning. Several examples of such devices follow.

U.S. Pat. No. 4,807,626 to McGirr discloses a basket-type stone extractor wherein a collapsible cage is extended within the body to wrap and enfold a stone. However, such devices are difficult to operate because the cage cannot grasp a stone from the same direction in which it approaches the stone. Thus, the cage must somehow be positioned adjacent to the stone, and then be laterally moved to enfold the stone. This can be very time-consuming and is not suitable for multiple stones present in a gallbladder.

U.S. Pat. No. 4,509,517 to Zibelin illustrates endoscopic pistol forceps for grasping and crushing or removing kidney stones. The end of the barrel of the device has two platelike opposable jaws, somewhat like the jaws of scissors, which pivot in the same plane so that their edges may be brought together on a stone. However, due to the flattened shape of the jaws and the small area of the edges which are to contact the stone, it is relatively easy for the stone to slip out from between the edges of the jaws. Therefore, repeated tries are often necessary to grasp a stone. The same is true of forceps such as those illustrated by U.S. Pat. No. 2,034,785 to Wappler. Additionally, endoscopic pistol forceps such as that of Zibelin and U.S. Pat. No. 2,113,246 to Wappler are generally difficult for an operator to precisely position, and they often require several tries before the forceps can be accurately located adjacent to smaller stones.

A final type of stone removal device is the stone forceps, which generally takes the form of tongs or a scissors-like jawed instrument. Despite their relative simplicity, these forceps have been the preferred stone removal devices for nearly a century because they are inexpensive to manufacture and easy to position, operate, and clean. A summary of several prior art stone forceps follows.

A good example of one type of stone forceps is the No. 600-520 Jarit stone extractor (Jarit Instruments, Hawthorne, N.Y.). The Jarit stone extractor is a scissors-like forceps having handles at one end, a central pivot, and slender upper arms terminating in bulbous, bowl-like tips which grow wider further from the handles. The tips have a fairly wide and deep bowl, the depth being approximately 1 to 2 times the thickness of the upper arm at the juncture of the upper arm and tip. This greater depth enables smaller stones to be fully enclosed between the tips and withdrawn from the gallbladder. The tips additionally have a serrated rim to better grip stones. However, the Jarit stone extractor is not well suited for breaking stones. The juncture between the upper arms of the forceps and the tips is too slender to withstand substantial stone-crushing pressures. Also, owing to the depth of the bowls, a stone which is gripped between the tips and which presses against the floors of the bowls generates moment forces at the upper arms which promote bending of the tips relative to the upper arms. Because larger stones or stone fragments grasped between the tips may be covered by the broad portion of the tips but exposed near the narrow portion, sharp edges of the stone may be exposed adjacent the upper arms of the forceps, causing cuts to the gallbladder during withdrawal of the forceps. The serrated rims of the tips can also catch on the gallbladder lining and possibly tear it, causing spillage of bile and debris. Finally, the broad leading edge of the tips makes the closed stone extractor difficult to insert within the small opening in the gallbladder neck when the neck is extracted from an abdominal port site.

Good examples of a second type of stone forceps are illustrated in U.S. Pat. No. 4,088,134 to Mazzariello, U.S. Pat. No. 4,300,584 to Furihata, and by the Blake gallstone forceps (Catalog No. 30-4278, Codman Catalog of Surgical Instruments, 1984). These forceps illustrate tips which include central apertures therein. Such apertures allow irregularly-shaped stones to be better grasped between the tips, but they are not as useful for crushing stones. These types of forceps were primarily designed and are generally recommended for delicately grasping and removing stones from tubular structures, such as bile ducts, and they lack the structural strength and mechanical advantage to crush stones. They are generally very narrow and tend to perforate the gallbladder, causing spillage of bile and debris. Small stones or stone fragments can fall through the apertures, requiring that the operator have smaller forceps on hand to accommodate the smaller stones. Additionally, the apertures in the forceps may expose sharp edges of stones or stone fragments, and surrounding tissue may be cut by these sharp edges when the forceps are withdrawn.

In summary, the stone extraction forceps of the prior art suffer from several disadvantages. They are often not well suited for crushing larger stones because their tips are subject to bending or because they do not allow the mechanical advantage necessary to crush stones. When the forceps are made with the proper size for crushing larger stones, the forceps tend to be so large that the port sites must be enlarged to accommodate the tool. The prior art forceps are often not well suited to grasp small stones either because such stones fall through apertures in the tips, or because serrated edges on the tips scrape and traumatize the gallbladder during retrieval of small stones. When the prior art forceps are sized to accommodate small stones well, they are generally configured with such small and slender tips that the likelihood of puncturing the gallbladder is greatly increased. Because the prior art forceps are generally configured for extraction of either larger stones or smaller stones, the operator requires two or more different forceps on hand during an operation to insure that all sizes and shapes of stones can be accommodated. Even then, the range of tools available is simply poorly suited to the task at hand. Attempts to trade up or down in forceps size or design during the operation increase operation times. Also, the prior art forceps may allow cuts or tears to the patient's gallbladder if they include apertures at the tips which expose sharp edges of stones or stone fragments, or if the tips are shaped in such a way that sharp edges are exposed at the leading edge of the tips during withdrawal of the forceps.

In view of the aforementioned disadvantages of the prior art, there is a need in the art for stone forceps which are well suited for the grasping, crushing, and removal of both large and small stones and which allow removal of stones without perforating, scraping, or tearing the gallbladder, yet are easily inserted into the small opening in a gallbladder neck which has been brought through an abdominal port site during laparoscopic cholecystectomy.

SUMMARY OF THE INVENTION

The present invention is directed to gallbladder stone forceps comprising a pair of upper arms, each upper arm including a tip and pivot means located opposite the tip for pivotally attaching one upper arm to the other upper arm. The tip includes a concave inner face, a teardrop-shaped rim bounding the inner face, and an outer face opposite the inner face. The inner face includes a distal narrow region, a central wide region, and a proximal narrow region, the distal narrow region being located further from the pivot means than the proximal narrow region. One upper arm engages the other upper arm at the pivot means so that the respective tips of each upper arm may be pivoted about the pivot means in opposing relation so that the rims of the respective tips may be brought into contact.

The present invention is also directed to gallbladder stone forceps comprising a pair of elongated members, each member including a handle, an opposing tip, and pivot means connecting the intermediate portions of the members for moving the tips toward each other to a closed position and away from each other to an open position by actuation of the handles. The tip of each member includes a concave inner face, a convex outer face, and a teardrop-shaped rim having a distal narrow region furthest from the handle, a central wide region, and a proximal narrow region nearest the handle. The maximum inward spacing between each inner face and its respective rim is no greater than the minimum diameter of its respective member.

The present invention is further directed to gallbladder stone forceps comprising two members, each member including an upper arm terminating at a tip, a lower leg connected to the upper arm and terminating at a handle, and pivot means located between the upper arm and lower leg of each member for pivotally attaching the members. The tip of each upper arm includes a concave inner face, a rim surrounding the inner face, and a convex outer surface opposing the inner face. Each upper arm is bowed outward between the handle and the tip so that the handles may be actuated to pivot the upper arms about the pivot means in opposing relation so that the rims of the respective tips may be brought into spring-biased contact.

The stone forceps of the present invention addresses the disadvantages of the prior art stone removal devices, and it additionally provides advantages which are new and unexpected to the art. The stone forceps are equally well suited for grasping, crushing, and removal of both large and small stones and stone fragments without the need for additional forceps or other tools. It is believed that the gallstone forceps of the present invention are superior to any known stone forceps of the prior art in terms of ease of utility, more specifically, in their ability to grasp and crush stones having a wide variety of sizes and subsequently remove the stones or fragments without puncturing, tearing, or cutting the gallbladder, while still being very easy to insert into the opening made in the gallbladder when it is being extracted through an abdominal port site during laparoscopic cholecystectomy. Additionally, because the forceps are equally well suited for the grasping and removal of small and large stones, the operator may speedily remove a variety of differently-sized stones without needing to trade up or down in forceps size.

Further features, advantages, and objects of the invention will be apparent from the following detailed description of the invention in conjunction with the associated drawings.

BRIEF DESCRIPTION OF THE DRAWINGS

FIG. 1 is a from elevated view of the stone forceps of the present invention, shown in closed position.

FIG. 2 is a cross-sectional view of the tips of the stone forceps, shown in closed position and taken at line 2—2 in FIG. 1.

FIG. 3 is a side elevated view of the stone forceps of the present invention, shown in closed position.

DETAILED DESCRIPTION OF THE INVENTION

Figure 6:
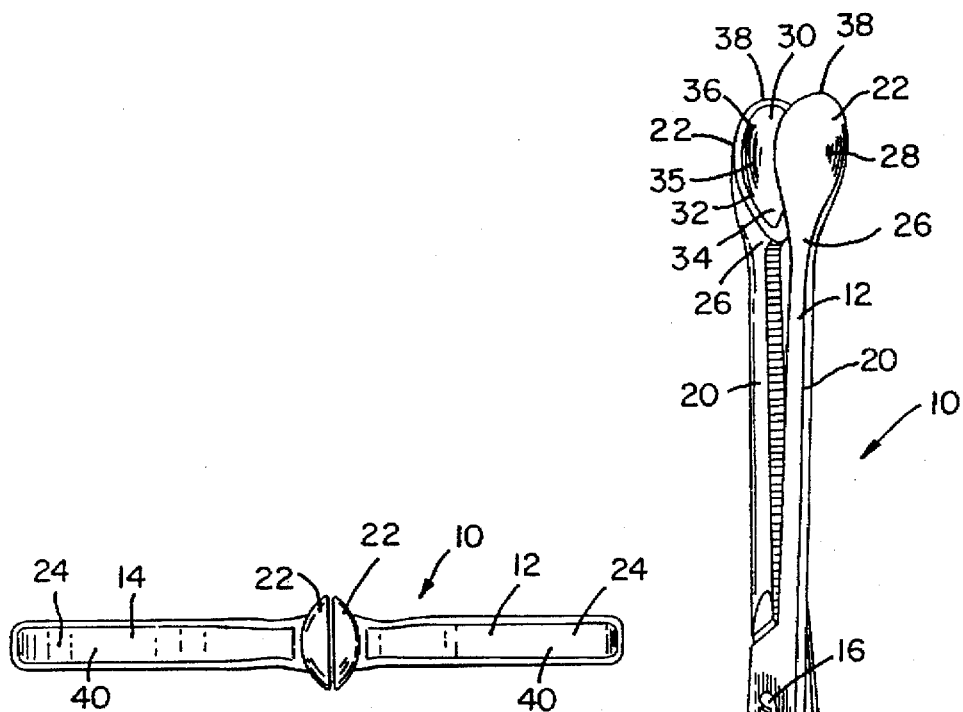
FIG. 6 is a perspective view of the stone forceps of the present invention, shown in open position.
Figure 4:
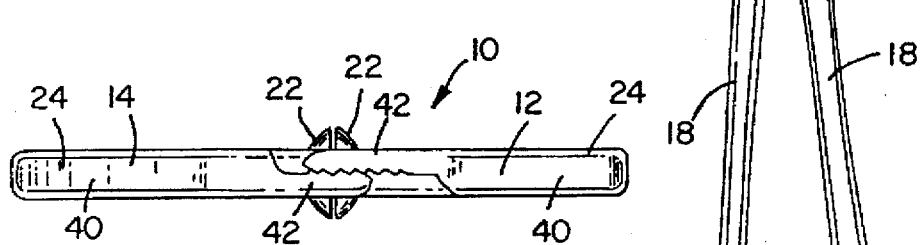
FIG. 4 is a top plan view of the stone forceps of the present invention, shown in closed position.
Figure 5:
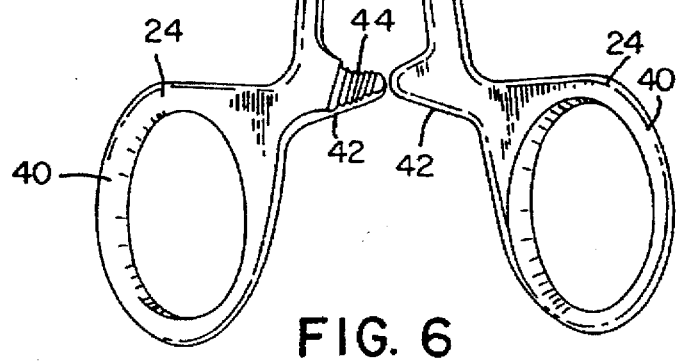
FIG. 5 is a bottom plan view of the stone forceps of the present invention, shown in closed position.

With reference to the drawings, wherein the same or similar features are designated with the same reference numerals throughout, FIG. 1 illustrates a front view of the stone forceps 10 of the present invention. The stone forceps 10 includes three main parts: a first member 12, a second member 14, and pivot means 16, i.e., a screw, for rotatably attaching the first member 12 to the second member 14. Each member 12 and 14 includes a lower leg 18 and an upper arm 20 situated on opposite sides of the screw 16. Each upper arm 20 includes a tip 22, and each lower leg 18 includes a handle 24. The handles 24 may be actuated to opposably pivot the tips 22 about the screw 16. The tips 22 can thereby be moved away from each other in symmetrical fashion, and can also be brought together to meet in a complementary manner. The tips 22 and handles 24 will each be discussed in turn below.

Each tip 22 is attached to its respective upper arm 20 at a wedge-shaped neck or juncture 26. The outer surface 28 of each tip 22 has a substantially rounded, teardrop-shaped profile, as best illustrated by FIG. 3. As shown best by FIGS. 2 and 6, each tip 22 has a rounded, slightly convex outer surface 28, that is, the tips 22 are each slightly thicker than the upper arms 20 (the thickness being measured along a direction perpendicular to the length of the forceps 10 in FIG. 1). Each tip 22 includes a concave inner face 30 and a rim 32 which bounds the inner face 30. The rim 32 surrounds an elongated depression 33 having a semi-ovoidal contour generally similar to that of the outer surface of an egg which has been bisected at a plane parallel to its longitudinal axis. This depression 33 incudes a proximal narrow region 34 at the juncture 26, a centrally-located wide region 35, and a distal narrow region 36 at the leading edge 38 of the tips 22 which is slightly smaller than the proximal narrow region 34. The distal narrow region 36 gives the leading edge 38 of the tips 22 a slight taper or point. Several features of these tips 22 warrant further detailed description owing to the advantages which their structure confers.

First, as shown best by FIGS. 1 and 6, it is preferred that the tips 22 have a slightly convex outer surface 28, and that the tips 22 be slightly thicker than the upper arms 20. The thicker tips 22 and convex outer surface 28 provides an advantage in that the resultant larger cross-sectional area of the tips 22 makes it more difficult for the tips 22 to be accidentally punctured through the walls of the gallbladder. This avoids the likelihood of puncture inherent in prior art forceps wherein the upper arms and tips have a generally uniform thickness and non-convex outer surface.

Second, the elongated oval shape of the tips 22 confers certain advantages during insertion and removal of the forceps 10 within gallbladders. Initially, the distal narrow region 36 makes the tip 22 easier to insert within the opened gallbladder neck than prior art forceps which have a wider, blunt leading edge or a generally bulbous tip, e.g., the Jarit stone extractor forceps. Also, while the distal narrow region 36 allows easy insertion of the stone forceps 10 into a gallbladder, the central wide region 35 protects the gallbladder from sharp edges of stones or stone fragments as the stone forceps 10 is being withdrawn from the gallbladder. During withdrawal of the forceps 10, the wide region 35 shields the gallbladder from any stone edges which may possibly be protruding from between the rims 32 of the tips 22 at the distal narrow region 36. This is to be contrasted with stone forceps of the prior art which include tips which only have narrow regions nearer to the pivot means (e.g., the Jarit stone extractor forceps); in such prior art forceps, sharp stone edges can be left exposed at this narrow region and can cause lacerations in the gallbladder because the narrow region leads the remainder of the tip during withdrawal.

Third, the spoon-like, semi-ovoidal depressed inner faces 30 also confer certain operational advantages to the stone forceps 10. Because stones are frequently slippery, it sometimes occurs that when a stone is being gripped in prior art forceps, the stone slides between the tips and towards the leading edge of the tips as the upper arms are brought together. The stone can slide along the tips or the rims of the tips until it eventually falls out from between the tips. If the stone is especially slippery and the tips are being closed with substantial force, the stone can even shoot forward from between the closing tips like a projectile. This occurs most often with larger stones because when such stones do not fit within the depressed inner faces of the prior art forceps, they often ride along the rims as the tips close about the stone. This is especially common in the prior art forceps wherein the depressions on the tips grow wider as the distance from the handles increases (i.e., the rims grow farther apart rather than closer together). Because such rims relieve the pressure on the stone rather than increasing it as the stone slides further away from the handles, the stone may accelerate toward the tips, and it is more likely to shoot out from between the tips. This is also common where the stone is so large that it protrudes from between the rims and pulls against the gallbladder walls during withdrawal of the forceps, in which case the gallbladder may pull the stone from between the tips.

In contrast, the tips 22 of the stone forceps 10 of the present invention taper at the distal narrow region 36 so that opposing sides of the rim 32 grow closer together as the distance from the handles 24 increases. Thus, if a stone begins to slide forward, in the direction away from the handles 24, the narrowing opposing sides of the rim 32 in the distal narrow region 36 will increase the pressure on the stone rather than decreasing it. This greatly decreases the likelihood that the stone will fall from or be ejected from between the tips 22.

Fourth, each tip 22 has a preferred aspect ratio, i.e., a preferred relationship between its height, depth, and width dimensions. It is believed that this aspect ratio provides an optimal size-to-strength relationship for the tips 22 and allows greater ability to crush larger stones without damaging the forceps 10, while still providing a tip 22 configuration which works well for retrieving small stones. Features of this aspect ratio are characterized as follows.

Initially, it is preferred that the maximum width of the tips 22 at the wide region 35 is between three and six times the maximum depth of the inner faces 30, with the most preferable width to depth ratio being approximately 4:1. This ratio has been found to provide an optimal tip 22 configuration for the purposes of both grasping and crushing stones. When the width to depth ratio is increased above 6:1, the grasping function of the tips 22 is impaired because the depressions 33 on the tips 22 are not sufficiently concave to allow firm grasping of the stones in the slippery environment of the abdominal cavity. On the other hand, when the ratio is decreased below 3:1, the crushing function of the more concave tips 22 is degraded because stones are more likely to contact only the rim 32, rather than the inner faces 30 or the inner faces 30 and rim 32. The tips 22 thereby fail to present a single concentrated area where crushing force may be exerted on a stone. Additionally, the rim 32 may "trim the edges" off of stones which are only slightly larger than the tips 22, and thereby cause numerous sharp edges to spray from the tips 22 when the main portion of the stone slips between the tips 22 and the edges break away from the main portion of the stone. These small, sharp edges can be difficult to locate and retrieve.

Additionally, each tip 22 preferably has a maximum width at the wide region 35 of no greater than approximately four times the minimum diameter of the upper arm 20. Wider tips 22 increase the possibility that crushing forces are exerted on the tips 22 away from the axis of the upper arms, thereby creating unwanted torque along the axis of the upper arms 20 and possible bending or breaking.

Finally, and in any case, the depressions 33 on the inner faces 30 should have a maximum depth which is less than approximately the minimum diameter of the upper arm 20. With shallower inner faces 30, there is a lesser likelihood that moment forces exerted on the inner faces 30 will cause bending of the tips 22 relative to the remainder of the upper arms 20. When deeper inner faces are provided, as in the stone forceps of the prior art, the grasping or crushing of stones produces forces at the deepest points on the inner faces. Because these forces are exerted at points further from the axis of the upper arms, the moment forces are greater. This increases the likelihood that the tips may bend with respect to the upper arms, particularly at the juncture between the upper arms and the tips.

Fifth, as best illustrated by FIG. 2, the inner faces 30 preferably slope continuously inward from the rims 32. While apertures could be added to each tip 22, i.e., apertures leading from the inner face 30 to the outer surface 28, it is preferable that the outer surface 28 and inner face 30 instead be continuous surfaces. This increases the versatility of the stone forceps 10 insofar as it allows even very small stones to be grasped without falling out through an aperture and between the tips 22. The lack of apertures also prevents the possibility that a sharp edge of a stone will protrude through an aperture and cause lacerations to a gallbladder as the forceps 10 is withdrawn.

Sixth, smooth rims 32 are preferable because serrated rims merely increase the chance of trauma within a gallbladder when the tips 22 are in an open position and the forceps 10 is moved within the gallbladder. Additionally, if the tips 22 should become bent with respect to the upper arms 20, such serrations may become prominently exposed and may even cause trauma when the tips 22 are moved within the gallbladder in a closed state.

Each member 12 and 14 is configured to be substantially linear, that is, the lower leg 18 and upper arm 20 of each member 12 and 14 are nearly coaxial. However, as illustrated best by FIG. 1, the upper arms 20 are each slightly bowed between the pivot means 16 and the tip 22 so that the upper arms 20 are slightly separated at this point. Because of this separation, the upper arms 20 spring-bias the tips 22 together when the handles 24 are pulled tightly together. As a result, when the handles 24 are actuated to close the tips 22 tightly about a stone, the operator can "feel" the stone owing to the spring-like resistance felt at the handles 24. When the handles 24 are brought together to such an extent that the upper arms 20 straighten and abut in a parallel linear relationship, this spring-like resistance is no longer felt at the handles 24. Because the operator can see or sense how closely together the handles 24 are, and the operator can also feel how tightly the tips 22 grasp a stone owing to the extent of "springiness" felt at the handles 24, the bowed upper arms 20 can give the operator some indication of the size and shape of a stone as it is being grasped. The spring-biasing of the tips 22 by the bowed upper arms 20 is also advantageous insofar as it tends to force stones to slide from the proximal and distal narrow regions 34 and 36 of the depression 33 into the wide region 35 after the stones are gripped, thereby providing the tips 22 with a firmer grasp of the stones.

If desired, either the lower leg 18 or upper arm 20 can be curved in a direction away from the general plane of the forceps 10 to allow the operator to reach into places where straight forceps 10 would cause problems with either reach or visibility.

For better mechanical advantage and easier crushing of stones, it is preferable that the lower leg 18 be somewhat longer than the upper arm 20, with the ratio of upper arm 20 length to lower leg 18 length being approximately 3:5 to 2:3. This provides a 30–40% increase in the gripping force between the tips 22 as compared to the force applied at the handles 24.

The first member 12 and second member 14 are preferably identical, as shown in FIGS. 1 and 3–6. This allows one type of member to be mass-produced, and then two members can then be combined to complete the stone forceps 10.

In the preferred embodiment of the forceps 10, the handles 24 include finger loops 40 and wings 42 with ridges and grooves 44 thereon. The finger loops 50 are suitably configured to accommodate any size of finger. The wings 42 allow the operator to lock the members 12 and 14 in place when the ridges and grooves 44 on the opposing handles 24 are snapped together in complimentary fashion. The innermost ridges and grooves 44 on the wings 42 are located close to the loops 40 so that when they are engaged, the "bow" in the upper arms 20 is no longer present, and the upper arms 20 abut in a linear parallel relationship. The wings 42 may be disengaged by the operator flexing his or her hand such that each wing 42 is lifted off of the other. Thus, the operator may easily pivot the members 12 and 14 with respect to each other and lock and unlock the members 12 and 14 together with the use of only one hand.

The forceps 10 has preferred dimensions. Each member 10 and 12 has a length of approximately 14 cm from the juncture of the loops 40 and the lower legs 18 to the tips 22.

The lower legs have a preferred length of approximately 11 cm, and the upper legs have a preferred length of approximately 7 cm. The tips 22 preferably have a length of no greater than approximately 2 cm in the direction parallel to the upper arms 20, a width of no greater than 1 cm at the wide region 35, and a thickness of no greater than approximately 0.2 cm so that the maximum thickness of the combined tips is no greater than approximately 0.4 cm during insertion of the tips 22. The maximum depth and width of the depression 33 is preferably about 0.2 cm and 0.8 cm respectively. The depression 33 has a length of approximately 1.6 cm, with the maximum width of the depression 33 occurring at approximately 0.6 cm from the leading edge 38 of the tips 22 and 1 cm from the juncture 26 (i.e., the distal narrow region 36 below the widest point of the depression 33 is approximately half the size of the proximal narrow region 34). The rim 32 is uniformly approximately 0.1 cm wide except near the juncture 26, where it is slightly wider. Below the juncture 26, the upper arms 20 have a minimum diameter of approximately 0.25 cm at their narrowest point.

The forceps 10 are preferably made of stainless steel or a similar sterilizable and corrosion-proof metal, though plastic, wooden, ceramic or other materials could conceivably be used instead. The material used for the forceps 10 should be ductile enough to allow the bowed upper arms 20 to be spring-biased together, but should not be malleable enough to allow the upper arms 20 to become permanently bent after they are flexed or to allow the ridges and grooves 44 on the wings 42 to be easily worn.

It is understood that while a screw 16 is used as the pivot means in the preferred embodiment illustrated in FIGS. 1-6, other types of pivot means may be used instead. The screw 16, or any other removable fastener which engages an aperture in each member, allows the stone forceps 10 to be easily dissembled for cleaning in the event that matter accumulates between the members 12 and 14 near the pivot means. However, it is understood that the pivot means could instead comprise a pin extending from either member and engaging an aperture in the opposing member, or apertures in both members which are both engaged by a separate pin or fastener, or any other type of pivot means known to the art.

It is also understood that many of the advantages of the forceps 10 could be realized if the tips 22 and upper arms 20 of the forceps 10 were used in conjunction with other embodiments of surgical grasping devices, e.g., tongs or tweezers-type pincers, pistol-type endoscopic pincers, and the like. In short, it is understood that the specific embodiment of the members 12 and 14 illustrated above, and/or the handles 24 illustrated therein, are not necessary to realize all of the advantages presented by the tips 22. As an example, the pivot means can take the form of no more than a flexible bridge between two attached upper arms 20. In such an embodiment, the operator may grasp the upper arms 20 to manipulate the tips 22 in a manner similar to tongs or tweezers.

Finally, it is understood that the invention is not confined to the particular construction of parts and uses described and illustrated above, and rather the invention embraces such modified embodiments that come within the scope of the following claims. Further, it is understood that in these claims, means plus function clauses are intended to cover the structures described herein as performing their recited function and also both structural equivalents and equivalent structures. As an example, though a nail and a screw may not be structural equivalents insofar as a nail employs a cylindrical surface to secure parts together whereas a screw employs a helical surface, in the context of fastening parts, a nail and a screw are equivalent structures.

What is claimed is:

1. Gallbladder stone forceps comprising:
    a pair of upper arms, each upper arm including a tip and pivot means located opposite the tip for pivotally attaching one upper arm to the other upper arm, each upper arm having a minimum cross-sectional area situated between the tip and the pivot means,
    wherein the tip includes a concave inner face, a teardrop-shaped rim bounding the inner face, and an outer face opposite the inner face,
    and further wherein the inner face includes a distal narrow region at which the rim defines a generally rounded shape, a proximal narrow region at which the rim defines a generally "V"-shaped angle, and a central wide region resting between the distal narrow region and the proximal narrow region, the inner face having maximum width at the central wide region, the distal narrow region being located further from the pivot means than the proximal narrow region, the distal narrow region having a maximum width corresponding to the maximum width of the central wide region and a maximum length greater than one-half of the maximum width of the central wide region,
    and further wherein a maximum inward spacing between each inner face and its respective rim is no greater than approximately the minimum cross-sectional area of its respective under arm,
    and further wherein one upper arm engages the other upper arm at the pivot means so that the respective tips of each upper arm are pivotable about the pivot means in opposing relation so that the rims of the respective tips are movable into contact.

2. The gallbladder stone forceps of claim 1 wherein an area of the distal narrow region is smaller than an area of its respective proximal narrow region.

3. The gallbladder stone forceps of claim 1 wherein an area of the distal narrow region is approximately half the size of an area of its respective proximal narrow region.

4. The gallbladder stone forceps of claim 1 wherein a maximum width of the wide region of each tip is less than approximately four times greater than a minimum cross-sectional area of its respective upper arm.

5. The gallbladder stone forceps of claim 1 wherein a maximum width of the wide region of each tip is between approximately three and six times greater than a maximum inward spacing between its respective inner face and its respective rim.

6. The gallbladder stone forceps of claim 1 wherein a maximum width of the wide region of each tip is approximately four times greater than a maximum inward spacing between its respective inner face and its respective rim.

7. The gallbladder stone forceps of claim 1 wherein each rim is generally smooth.

8. The gallbladder stone forceps of claim 1 wherein the upper arms are bowed outward between the tip and the pivot means to thereby spring-bias the tips together when the rims of the respective tips are brought into contact.

9. The gallbladder stone forceps of claim 1 further comprising two lower legs each connected to respective upper arms.

10. The gallbladder stone forceps of claim 9 wherein each lower leg includes a handle opposite the pivot means.

11. The gallbladder stone forceps of claim 9 wherein each lower leg is longer than its respective upper arm.

12. The gallbladder stone forceps of claim 9 wherein the ratio between the length of each upper arm and its respective lower leg is between approximately 3:5 to approximately 2:3.

13. Gallbladder stone forceps comprising:

a pair of elongated members, each member including a handle, an opposing tip, and pivot means connecting the intermediate portions of the members for moving the tips toward each other to a closed position and away from each other to an open position by actuation of the handles, each member having a minimum cross-sectional area situated between the tip and the pivot means, wherein the tip of each member includes a concave inner face, a convex outer face, and a teardrop-shaped rim having a distal generally rounded narrow region furthest from the handle, a proximal generally "V"-shaped narrow region nearest the handle, and a central wide region between the distal and proximal narrow regions, the inner face having maximum width at the central wide region, and wherein the rim in the distal narrow region has maximum spacing from the central wide region by a distance greater than one-half of the maximum width of the inner face, and further wherein a maximum inward spacing between each inner face and its respective rim is no greater than the minimum cross-sectional area of its respective member.

14. The gallbladder stone forceps of claim 13 wherein a maximum width of each concave inner face is between approximately three and six times greater than a maximum inward spacing between that concave inner face and its respective rim.

15. The gallbladder stone forceps of claim 13 wherein each member is bowed outward between its respective tip and the pivot means to thereby allow one tip to be spring-biased against the other tip when the tips are in the closed position.

* * * * *